(12) United States Patent
Keenan

(10) Patent No.: US 7,547,384 B2
(45) Date of Patent: Jun. 16, 2009

(54) ELECTROCHEMICAL DETECTOR SYSTEMS

(75) Inventor: Elizabeth Ann Keenan, Bolton (GB)

(73) Assignee: Millipore Corporation, Billerica, MA (US)

( * ) Notice: Subject to any disclaimer, the term of this patent is extended or adjusted under 35 U.S.C. 154(b) by 741 days.

(21) Appl. No.: 10/508,482

(22) PCT Filed: Apr. 2, 2003

(86) PCT No.: PCT/GB03/01445

§ 371 (c)(1),
(2), (4) Date: Feb. 17, 2005

(87) PCT Pub. No.: WO03/087398

PCT Pub. Date: Oct. 23, 2003

(65) Prior Publication Data

US 2005/0126908 A1 Jun. 16, 2005

(30) Foreign Application Priority Data

Apr. 4, 2002 (GB) ................... 0207813.7

(51) Int. Cl.
*G01N 27/327* (2006.01)
(52) U.S. Cl. ................... 205/778; 204/403.01
(58) Field of Classification Search ........... 205/778; 204/403.01; 422/44–48
See application file for complete search history.

(56) References Cited

U.S. PATENT DOCUMENTS

| | | | |
|---|---|---|---|
| 4,267,053 A | 5/1981 | Hashino et al. | 210/650 |
| 4,335,206 A | 6/1982 | Wilkins et al. | 435/34 |
| 4,547,289 A | 10/1985 | Okano et al. | 210/652 |
| 4,714,556 A | 12/1987 | Ambrus et al. | 210/638 |
| 4,735,899 A | 4/1988 | Stuart et al. | 435/29 |
| 5,139,668 A | 8/1992 | Pan et al. | 210/321.8 |
| 5,139,881 A | 8/1992 | Henis et al. | 424/488 |
| 5,650,506 A | 7/1997 | Woodard et al. | 536/25.4 |
| 5,871,649 A | 2/1999 | Ofsthun et al. | 210/645 |
| 5,895,573 A | 4/1999 | Scharstuhl | 210/321.87 |
| 6,270,674 B1 | 8/2001 | Baurmeister et al. | 210/649 |
| 6,562,583 B1 | 5/2003 | Herbig et al. | 435/34 |
| 6,750,031 B1 | 6/2004 | Ligler et al. | 435/7.93 |
| 2002/0072103 A1* | 6/2002 | Matsumoto et al. | 435/200 |
| 2003/0155557 A1* | 8/2003 | Tierney | 252/500 |
| 2003/0166296 A1* | 9/2003 | Morrison et al. | 436/149 |

FOREIGN PATENT DOCUMENTS

| | | |
|---|---|---|
| DE | 197 50 215 | 2/1999 |
| DE | 198 14 715 | 10/1999 |
| EP | 0 302 949 | 2/1989 |

(Continued)

OTHER PUBLICATIONS

Proc. SPIE vol. 4265; pp. 65-74; Dalibor Hodko et al.; "Detection of Pathogens Using On-Chip Electrochemical Analysis of PCR Amplified DNA Molecules".

(Continued)

*Primary Examiner*—Alex Noguerola
(74) *Attorney, Agent, or Firm*—Nields, Lemack & Frame, LLC

(57) ABSTRACT

The present invention concerns methods for detecting microorganisms in a sample, and apparatus comprising hollow fibre filter membranes for same.

20 Claims, 3 Drawing Sheets

FOREIGN PATENT DOCUMENTS

| | | |
|---|---|---|
| EP | 0 439 212 | 7/1991 |
| FR | 2 809 969 | 12/2001 |
| GB | 2135902 | 9/1984 |
| GB | 2 352 652 | 2/2001 |
| WO | 87/03690 | 6/1987 |
| WO | 94/25848 | 11/1994 |
| WO | 96/04067 | 2/1996 |
| WO | 98/04675 | 2/1998 |
| WO | 00/23792 | 4/2000 |
| WO | 02/062941 | 8/2002 |

OTHER PUBLICATIONS

European communication dated Dec. 21, 2006.
European communication dated Sep. 5, 2007.
European communication dated Mar. 5, 2008.
Office actions dated Apr. 5, 2006, Jul. 12, 2006, Mar. 16, 2007, Nov. 5, 2007, Jul. 25, 2007, May 1, 2008 (corresponding U.S. Appl. No. 10/467,440).
Office actions dated Apr. 24, 2008 (corresponding U.S. Appl. No. 11/382,725).

* cited by examiner

ELECTROCHEMICAL DETECTOR SYSTEMS

As rigid product quality regulations become enforced within the food, water and beverage industry, it is becoming increasingly necessary to improve on the methods used to detect contaminants within product processes, since current methods are labour intensive and require long time periods to generate results. The ability to filter greater volumes using hollow fibre membrane technology (such as in WO 01/11006) provides a method of concentrating the number of contaminants from a much greater and more representative sample volume and increases the level of sensitivity achieved. The limitation to this technology is the method used to identify contaminants.

The requirement for the identification of a single cell within a volume of liquid eg. beer, water or fruit juice is limited by the current techniques applied. To increase the sensitivity of detection for microbial contamination in a sample, methods using biosensors, PCR (polymerase chain reaction), or immunological technology have been developed. However, these technologies all require the analysis and detection of contaminants from a small volume of the sample liquid (typically in ml-µl range), which is usually unrepresentative of the large volume of liquid being sampled (eg from a 20 000 L fermenter), often resulting in a failure to detect contaminants in the sample.

The potential combination of the existing membrane technology seen in WO 01/11006 with newly developing nanoscale based systems would lead to increased sample handling with real time analysis capability. Typical nanoscale systems can utilise electrochemical technology, biosensor technology, nanowires, self-assembled monolayers (SAMs), and high sensitivity miniaturised detector systems. The incorporation of single or multiple fibre array detector systems combining wire electrochemistry or membrane surface coating technology and biosensor applications onto hollow fibre membrane would greatly facilitate the analysis and detection of contaminants for any given sample. The ability to accommodate reverse flow generation within the membrane filtration system enables biomolecules that have been undetected during the first filtration phase to be re-exposed to the detector surface, thereby increasing the detector sensitivity.

According to the present invention, there is a provided a method for detecting a micro-organism in a sample, comprising the steps of:
i) passing said sample through the sample inlet of a filter device comprising a plurality of hollow fibre filter membranes and at least one detector system, said membranes having first and second ends, an outer surface and an inner surface defining a lumen, said first end of each of said membranes being open and communicating with said sample inlet and flow through said second end of each of said membranes being restricted such that said sample mixture is filtered through said membranes, leaving a filtrand in said lumen of said membranes, said at least one detector system being at least partially contained within said lumen of said membranes;
ii) optionally resuspending said filtrand from said lumen of said membranes;
iii) detecting with said at least one detector system the presence of micro-organisms in said filtrand; and
iv) correlating the results of detection step (iii) with the presence of said micro-organism in said sample.

The method may comprise the additional step of detecting with at least one detector system the presence of micro-organisms in the sample mixture, before or during the filtration step.

The hollow fibre membranes may be composed of a variety of polymers such as polypropylene, polyethersulphone and cellulose acetate.

The detector system may be an electrochemical detector system and may comprise a plurality of electrodes. Examples of suitable electrodes include gold electrodes, and long chain polymer electrodes.

The detector system may be an electrochemical biosensor.

The surface of at least one of the electrodes of the detector system may be modified such that a plurality of first members of a specific binding pair depends therefrom.

A "Member of a Specific Binding Pair" is one of two different molecules, having an area on the surface or in a cavity which specifically binds to and is thereby defined as complementary with a particular spatial and polar organization of the other molecule. The members of the specific binding pair (sbp) are referred to as ligand and receptor (antiligand), sbp member and sbp partner, sbp members or the like. These are usually members of an immunological pair such as antigen-antibody, although the term does have a broader meaning encompassing other specific binding pairs, such as biotin-avidin, hormones-hormone receptors, nucleic acid hybrids (e.g. DNA-DNA, DNA-RNA, RNA-RNA), IgG-protein A.

The modification of the surface chemistry of either the gold or polymer electrode facilitates the attachment of biomolecules such as antibodies, enzymes and nucleic acids. These biomolecules may specifically interact with second members of the specific binding pair within the fluid stream (e.g. an antigen if the first member of the specific binding pair is an antibody), generating an electrically active complex which can be detected, amplified, quantitated and displayed using an amplifier, potentiostat, and computer (running appropriate data acquisition software) set-up.

The surface of at least one of the electrodes of a second detector system may be modified such that a plurality of first members of a second specific binding pair depends therefrom.

The surface of at least one of the electrodes of at least one additional detector system may be modified such that a plurality of first members of at least one additional specific binding pair depends therefrom. Since the use of additional specific binding pairs facilitates the specific detection of additional micro-organisms within the sample, the use of multiple electrodes (each coated with a different specific binding pair) within the filter device, would facilitate the specific detection of multiple micro-organisms within a sample.

The detector system may detect at least one of the group comprising: bioluminescence, electrochemical activity, fluorescence, chemi-luminescence, radiochemicals, radioisotopes, alpha particles, beta particles, gamma rays, antibody-antigen interactions, protein-protein interactions, protein-enzyme interactions, protein-nucleic acid hybrids, nucleic acid hybrids.

The filter device may comprise a plurality of hollow fibre filter membranes and at least one detector system, said membranes having first and second ends, an outer surface and an inner surface defining a lumen, said first end of each of said membranes being open and communicating with said sample inlet and flow through said second end of each of said membranes being restricted such that said sample mixture is filtered through said membranes, leaving a filtrand in said lumen of said membranes, said at least one detection system being at least partially contained within said lumen of said membranes.

The invention will be further apparent from the following description, with reference to the accompanying Figures, which show, by example only, forms of the filter device and testing methods.

Figure 1:
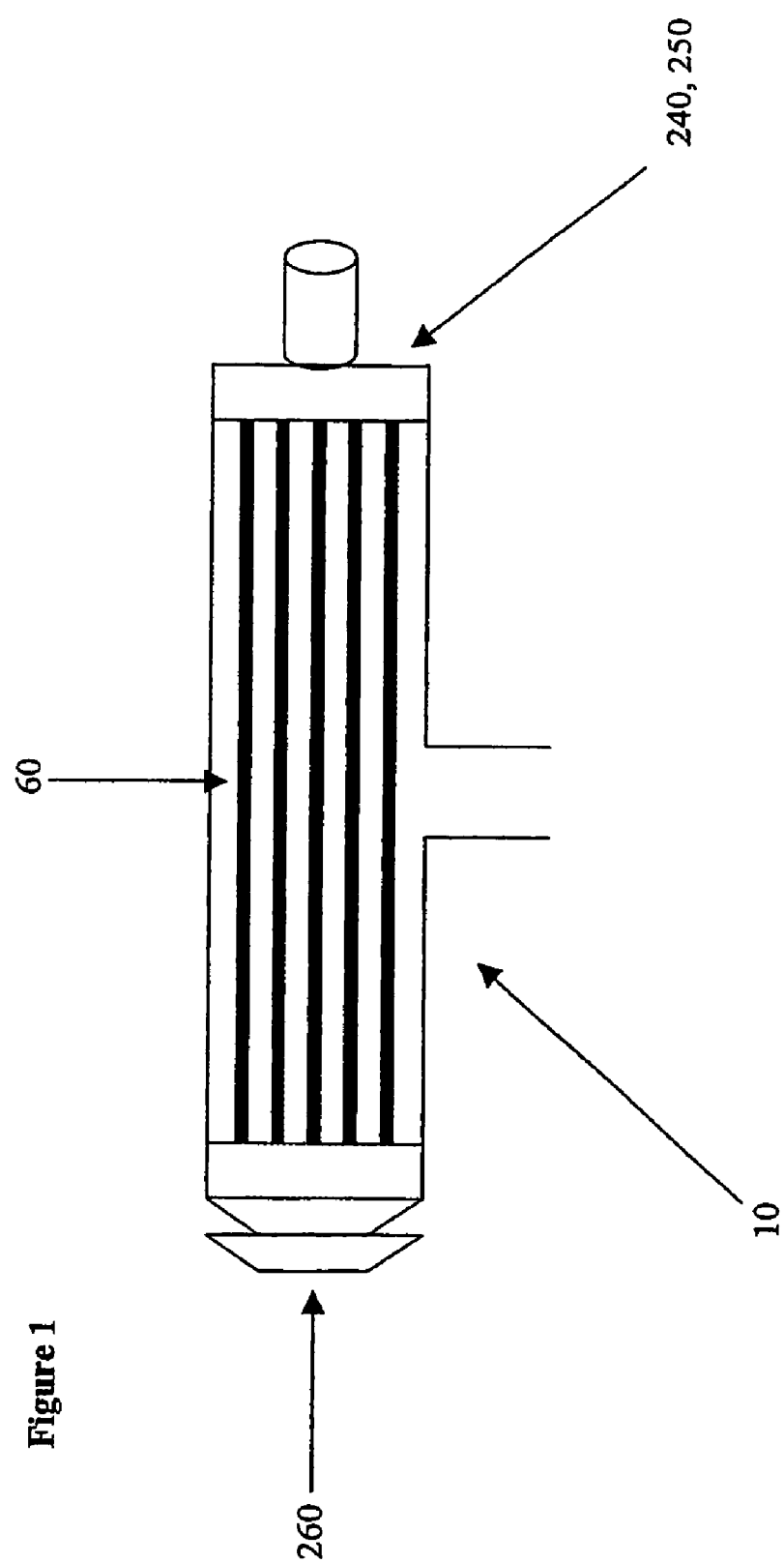
FIG. 1 shows a hollow fibre membrane filter device.
Figure 2:
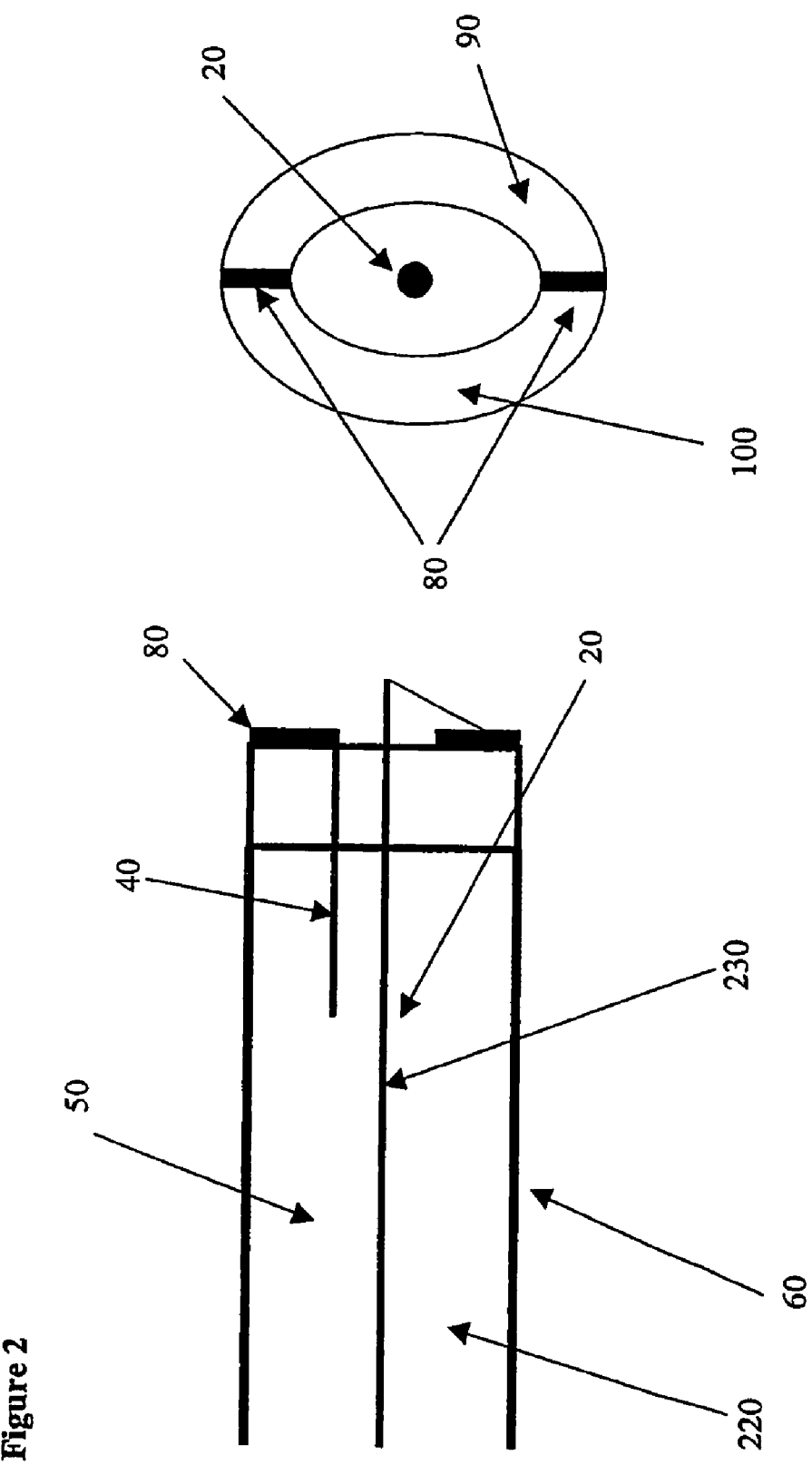
FIG. 2 shows a gold wire electrochemical detector.

In a first embodiment of the present invention the electrochemical detector system (10) may comprise a three electrode set-up where the electrodes are designated working (20), reference (30) and counter (40). The working electrode (20) is gold and runs through the lumen (50) of the hollow fibre membrane (60) (FIG. 2), the counter electrode (40) is placed partially into the lumen (50) of the membrane (ca 10 mm), and the reference electrode (30) is connected externally to the reference material (70) (test sample). The working and counter electrodes (20, 40) are then connected to a gold contact pad (80) which is located on the outer rim (90) of the hollow fibre housing (100) used to support the hollow fibre membranes (60) (FIG. 1). The contact pads (80) for both the working and counter electrodes (20, 40) are applied to the end of the hollow fibre housing (100) by screen printing during injection moulding of the filter housing. Other available procedures include standard photolithographic lift off procedures, and the use of silver conducting paint. After screen printing into the injection moulding of the end cap tool, the electrodes (20,40) are then connected to the contact pads (80) using silver conducting paint followed by connection of standard timed copper wires (130, 140) being connected to the electrode contact pads (80). The copper wires (130, 140) are connected at one end to a Molex crimp (150) which is slotted into a Molex Shell/PCB header (170). A direct connection is made from the Molex Shell/PCB header (170) to a pre-amp (180) using standard tinned copper wire (190). The pre-amp (180) is connected to a potentiostat (200) via an amplifier (210). A computer (215) is connected to the potentiostat (200).

Figure 3:
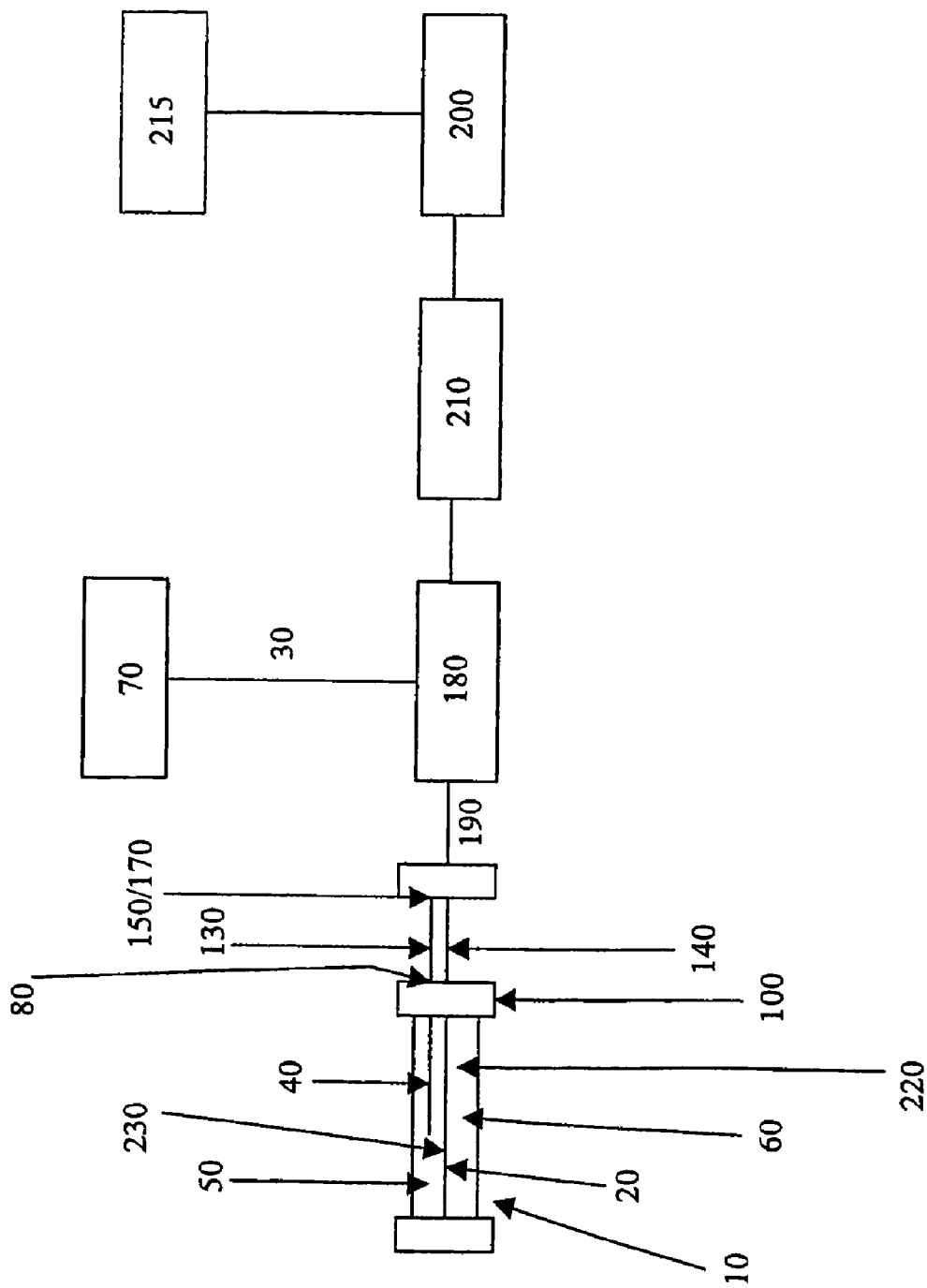
FIG. 3 shows a hollow fibre electrochemical detector set-up.

Potentiostats establish a specific potential across a metal-electrolyte interface, usually so that the current passed through the interface can be measured. Many potentiostats have the capability of operating as a galvanostat. In this form of operation a predetermined constant current may be forced through the metal electrolyte interface and the potential across it measured. The potentiostat can convert the signal into measurable data which is processed on a computer (215) running LabVIEW data acquisition software. The reference electrode (30) can be pseudo-floating, i.e. it can be connected externally to the pre-amp (180) and is not part of the filter device (10) (FIG. 3).

The use of an electrochemical detector using a bare gold wire allows for the detection (using linear sweep, cyclic voltammetry or chronoamperometry) of the most simple of electrically active analytes (e.g. protons for pH measurement).

In a second embodiment of the present invention, the sensitivity and selectivity of the detector system can be increased by converting the device into an electrochemical biosensor. A biosensor is generally a metal or polymer substrate with a modification to its surface chemistry, which allows for the immobilisation of a first member of specific binding pair e.g. biomolecules such as antibodies, enzymes and nucleic acids. These biomolecules then interact with second members of the specific binding pair within the fluid stream, generating an electrically active complex which can be detected electrochemically. In order to bind the first member of a specific binding pair, the surface of the gold electrode is modified by silinization, either through immersion into a silane solution, or alternatively by vapour deposition. Alternatively, self-assembled monolayers (SAMs) can be prepared using different types of molecules and different substrates—examples include alkylsiloxane monolayers, fatty acids on oxidic materials, and alkanethiolate monolayers. Alkanethiolate monolayers are especially useful since they adsorb with high efficiency to gold electrodes. Alkanethiolate is a molecule which is essentially an alkane chain, typically with 10-20 methyl units, and a head group with a strong preferential adsorption to the substrate used. The thiol molecules adsorb readily from solution onto the gold, creating a dense monolayer with the tail group pointing outwards from the surface. By using thiol molecules with different tail groups, the resulting chemical surface functionality can be varied within wide limits. It may be possible to chemically modify the tail groups by performing reactions after assembly of the SAM. For example, a simple incubation reaction of the thiol or silane activated gold wire with the appropriate antibody, enzyme, or DNA molecule can take place in order to achieve specific detection.

Another option for the production of a biosensor within the hollow fibre is to coat the entire inner surface of the hollow fibre with gold using vapour deposition. The thickness of deposition can be controlled to a depth of approximately 10 nm; this means the coating does not interfere with the filtration function of the hollow fibre. There are two methods for vapour deposition—chemical and physical. Upon completion of chemical deposition the gold is then coated with silanes or SAMs and a biomolecule and connected via contact pads (80) to the data handling system as described previously. Again different coatings on different fibres within the manifold allow for the detection of multiple analytes. The benefits to this methodology include no need to manipulate electrode wires through the membrane, increase the number of active sites for coating of specific biomolecules, increased sensitivity and increased surface area.

Recent developments in polymer chemistry now mean that it is no longer necessary to be restricted to metal based wires for conduction and electrochemistry. A range of recently developed long chain polymers (e.g. triisopropylsilyl) have been found to have considerable conductivities. The availability of chemical groups on the surface of the polymer means that proteins can be immobilised directly (e.g. in chemical reactions) onto the polymer wire without surface modification.

The hollow fibre membranes may be secured into a polymer casing using standard techniques as described in WO 01/11006. Following activation of the gold or polymer electrode (20) with a first member of a specific binding pair (antibodies raised against *E. coli* 0157 H7 or oligonucleotides specific for *Salmonella typhimurium*) the electrodes (20, 40) are fed into the lumen (50) of the hollow fibre membrane (60). The electrodes (20, 40) are then secured with silver conducting paint to the contact pads (80). For the initial filtration of the sample, the contact pads (80) connected to the pre-amp (180) are sealed such that the sample (220) is forced through the membrane (60) walls. During the filtration process the specific analyte interacts with the bound biosensor molecule (230) and generates a signal. However, the ability of the total analyte population to be detected on a single pass is limited and dependent on the specificity of the analyte/biosensor interaction. These limitations may be due to flow rate of the liquid across the bio-sensor or the surface area of the bio-sensor or the affinity of the analyte for the bio-sensor. The present invention allows for the repeat detection of analyte that failed to be detected on first passage. Analyte which is not detected is entrapped within the lumen of the hollow fibre membrane (60) due to the pore size restriction properties of the membrane. For example *E. coli* not bound to the anti-*E. coli* antibody coated electrode will not pass through the membrane (60) walls but will remain within the membrane (60) structure as a filtrand. The entrapped bacteria are easily dislodged from the membrane walls by a simple backflush mechanism, as described in WO 01/11006. To ensure that there is no re-uptake of filtrate the system must become open ended. The contact end cap (240) is replaced at this stage with a contact pad (80) that is not sealed i.e. liquid can pass through the length of the membrane (60) without being forced through the membrane walls. The backflush liquid (250) used can be a biological buffer such as PBS (phosphate buffered saline) or Tris-BDTA. The buffer is applied into the membrane via the sample entry port (260) using a syringe (not shown). Upon resuspension of the filtrand the micro-organism can be detected by the detector. This method facilitates the detection of a single micro-organism within a liquid stream, which can be applied to liquids such as beer, water, fruit juices in such areas as Clean In Place (CIP) rinse water testing, final product sterility and process control.

In a third embodiment of the present invention, multiple array detector systems are used to detect multiple micro-organisms at the same time. Within the food industry there are a number of micro-organisms that are screened for regularly within wash water and process lines, for example *Escherichia coli, Salmonella typhimurium* and *Listeria monocytogensis*. By coating separate gold or polymer electrodes with antibodies or oligonucleotides specific for the micro-organism a multiple detector can be prepared. A single wire for each of the specified microbes is fed into the hollow fibre membrane and the detector constructed as described previously. In order to determine the specific analyte being detected, different contact pads for each of the specific analytes is typically required. A computer is able to differentiate the data from each of the contact pads, such that if *E. coli* is present, a conductivity change is detected from the contact pad connected to this specific electrode. The presence or absence of another micro-organism is detected via the relevant contact pad.

In a fourth embodiment of the present invention, multiple micro-organisms may be detected using multiple electrodes combined with the use of secondary biosensor systems i.e. enzyme assay systems. The electrodes may be coated using SAMs with a specific antibody/DNA for the relevant microbe whereby a single electrode can be coated with either one specific antibody or DNA, or multiple antibodies or DNA. The coating of an electrode with SAMs is detailed below. Self assembled monolayers (SAMs) comprising various functionalised alkane thiols do not bind to one another. Their chemical interaction is with the gold surface. To bind various antibodies along a length of the electrode requires the use of different functional groups on the outer region of the SAM such as amine groups or carboxylic acid groups that will interact with the antibodies. For example if three antibody types were to be placed onto the electrode, each region of the electrode would be coated with the appropriate SAM (one region at a time). To prevent SAMs from binding out with the target region a priming agent or blocking agent (eg photoresist) would be used for specific and defined areas. The electrode would be immersed into the SAM solution for a defined time period (dependent upon the kinetics of the SAM). The next target region can then be coated in a similar manner. There will be no binding within the previous region from the second SAM solution. This can be repeated for the appropriate number of antibody regions. The antibodies can be bound to the SAM on the electrode by immersion within the specific antibody solution or a mixed antibody solution. The SAM with specific functional group for each antibody will only bind to its appropriate ligand.

Detection of antigen binding to an antibody, or nucleic acid hybridisation will be detected using the following methods:

Secondary antibody conjugates or nucleic acid-enzyme conjugates may be employed, wherein the electrode may be washed after sampling has been conducted. For example, detection of *E. coli* may be through the use of an anti-*E. coli*-luciferase secondary antibody conjugate which may be passed through the filter device, which may then bind to the bacteria immobilised on the electrode. When the substrate luciferin is passed through the filter device, the reaction may be detected by monitoring $CO_2$ generation, for example. In the same way, *Salmonella typhimurium* may be detected by using an anti-*S. typhimurium* alkaline phosphatase secondary antibody conjugate, such that phosphate release could be measured in the presence of an appropriate substrate. There are numerous enzyme/biosensor systems that can be adapted to this purpose.

Another method that can be used to detect antigen binding to an antibody, or nucleic acid hybridisation is direct measurement using specific redox potential of each antibody/antigen binding (or nucleic acid hybrids) as sampling is occurring ie real time analysis. This will require the specific redox potential to be determined for each complex prior to analysis such that a shift in potential can be directly related to a specific antigen binding or a specific nucleic acid hybridisation event.

Another method that can be used to detect antigen binding to an antibody, or nucleic acid hybridisation could be by using reference electrodes for each antibody/antigen complex or nucleic acid hybrid in order to obtain real time control analysis i.e. for each antibody or nucleic acid used there would be a reference electrode that may be fed into the detection unit which would give a real time reference output of the expected redox potential if the sample contains the specific antigen or nucleic acid target.

In a fifth embodiment of the present invention, multiple airborne bio/chemical warfare agents are detected in a single filtration unit, using multiple electrodes coated with different affinity ligands, for example using electrodes coated with antibodies raised against *Bacillus anthracis* (the agent causing anthrax), antibodies raised against Ebola virus, and acetylcholinesterase enzyme (for detection of chemical nerve agents such as VX and sarin). The collected air sample may be placed into a suitable buffer such as a mild organic solvent, saline solution or surfactant. The sarin/VX may dissolve within the appropriate buffer. The buffer may then be passed through the membrane unit where the bio/chemical warfare agents bind to their appropriate affinity ligand on the specifically coated electrodes. The detection would be as above.

Detectors can be prepared to recognise alterations in the levels of bio-luminescence, electrochemical activity, fluorescence using fluorophores, chemi-luminescence, radiochemicals such as alpha, beta and gamma particles, antibodies-antigen interaction, protein/enzyme interaction, nucleic acid hybridisation.

The invention claimed is:

1. A method for detecting a micro-organism in a sample, comprising the steps of:
   i) passing said sample through the sample inlet of a filter device comprising a plurality of hollow fibre filter membranes and at least one detector system, said membranes having first and second ends, an outer surface and an inner surface defining a lumen, said first end of each of said membranes being open and communicating with said sample inlet and flow through said second end of each of said membranes being restricted such that said sample mixture is filtered through said membranes, leaving a filtrand in said lumen of said membranes, said at least one detector system comprising an electrode which runs through said lumen of said membranes;

ii) optionally resuspending said filtrand from said lumen of said membranes;

iii) detecting with said at least one detector system the presence of micro-organisms in said filtrand; and iv) correlating the results of detection step (iii) with the presence of said micro-organism in said sample.

2. A method according to claim 1, step (i), additionally comprising the step of detecting with said at least one detector system the presence of micro-organisms in said sample.

3. A method according to claim 2, correlation step (iv) comprising correlating the results of detection step (i) and detection step (iii) with the presence of said micro-organism in said sample.

4. A method according to claim 1, 2 or 3, wherein said at least one detector system comprises a plurality of electrodes.

5. A method according to claim 4, wherein the surface of at least one of said electrodes of a first detector system has been modified such that a plurality of first members of a specific binding pair depends therefrom.

6. A method according to claim 4, wherein said filter device comprises first and second detector systems, wherein the surface of at least one of said electrodes of a first detector system has been modified such that a plurality of first members of a specific binding pair depends therefrom, and the surface of at least one of said electrodes of a second detector system has been modified such that a plurality of second members of a specific binding pair depends therefrom.

7. A method according to claim 4, wherein the surface of at least one of said electrodes of at least one additional detector system has been modified such that a plurality of first members of at least one additional second specific binding pair depends therefrom.

8. A method according to any one of claims 1-3, wherein said at least one detector system detects at least one of the group consisting: bio-luminescence, electro-chemical activity, fluorescence, chemi-luminescence, radiochemicals, radioisotopes, alpha particles, beta particles, gamma rays, antibody-antigen interactions, protein-protein interactions, protein-enzyme interactions, nucleic acid hybridisation.

9. A method according to claim 1, wherein said at least one detector system comprises at least one gold electrode.

10. A method according to claim 1, wherein said electrochemical detector system comprises at least one long chain polymer electrode.

11. A method according to claim 1, wherein said at least one detector system is an electrochemical biosensor.

12. A filter device comprising a plurality of hollow fibre filter membranes and at least one detector system, said membranes having first and second ends, an outer surface and an inner surface defining a lumen, said first end of each of said membranes being open and communicating with said sample inlet and flow through said second end of each of said membranes being restricted such that said sample mixture is filtered through said membranes, leaving a filtrand in said lumen of said membranes, said at least one detection system comprising an electrode which runs through said lumen of said membranes.

13. The filter device of claim 12, wherein said at least one detector system comprises a plurality of electrodes.

14. The filter device of claim 12, wherein said at least one detector system comprises at least one gold electrode.

15. The filter device of claim 12, wherein said at least one detector system comprises at least one long chain polymer electrode.

16. The filter device of claim 12, wherein said at least one detector system comprises an electrochemical biosensor.

17. The filter device of claim 12, wherein the surface of at least one of said electrodes of a first detector system has been modified such that a plurality of first members of a specific binding pair depends therefrom.

18. The filter device of claim 12, wherein said filter device comprises first and second detector systems, wherein the surface of at least one of said electrodes of a first detector system has been modified such that a plurality of first members of a specific binding pair depends therefrom, and the surface of at least one of said electrodes of a second detector system has been modified such that a plurality of second members of a specific binding pair depends therefrom.

19. The filter device of claim 12, wherein the surface of at least one of said electrodes of at least one additional detector system has been modified such that a plurality of first members of at least one additional second specific binding pair depends therefrom.

20. The filter device of claim 12, wherein said at least one detector system detects at least one of the group consisting: bioluminescence, electrochemical activity, fluorescence, chemi-luminescence, radiochemicals, radioisotopes, alpha particles, beta particles, gamma rays, antibody-antigen interactions, protein-protein interactions, protein-enzyme interactions, nucleic acid hybridization.

* * * * *